United States Patent
Larsen et al.

(10) Patent No.: US 10,238,400 B2
(45) Date of Patent: Mar. 26, 2019

(54) SOFT TISSUE DISPLACER TOOL WITH INCLINED GROOVE AND METHODS

(71) Applicant: DePuy Synthes Products, Inc., Raynham, MA (US)

(72) Inventors: Scott P. Larsen, West Chester, PA (US); Wamis Singhatat, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/835,763

(22) Filed: Mar. 15, 2013

(65) Prior Publication Data

US 2014/0276833 A1   Sep. 18, 2014

(51) Int. Cl.
*A61B 17/3205* (2006.01)
*A61B 17/16* (2006.01)
(Continued)

(52) U.S. Cl.
CPC .............. *A61B 17/16* (2013.01); *A61B 17/02* (2013.01); *A61B 17/17* (2013.01); *A61B 17/3205* (2013.01); *A61B 17/1615* (2013.01); *A61B 17/32053* (2013.01); *A61B 17/3472* (2013.01); *A61B 2017/00349* (2013.01);
(Continued)

(58) Field of Classification Search
CPC ..... A61B 17/3205; A61B 17/16; A61B 17/77; A61B 17/02; A61B 17/1615; A61B 2017/00349
USPC ....... 606/79–80, 96, 170–171; 408/214, 220, 408/227, 230, 226, 202, 241 S
See application file for complete search history.

(56) References Cited

U.S. PATENT DOCUMENTS 4,537,185 A * 8/1985 Stednitz ........................ 606/304
4,713,004 A   12/1987 Linkow et al.
(Continued)

FOREIGN PATENT DOCUMENTS

CN   202270078 U  * 6/2012
CN   102711633 A   10/2012
(Continued)

OTHER PUBLICATIONS

International Search Report issued for PCT/US2014/021501 dated Jun. 27, 2014, 6 pages.
(Continued)

*Primary Examiner* — Eric S Gibson
*Assistant Examiner* — Marcela I Shirsat
(74) *Attorney, Agent, or Firm* — Baker & Hostetler LLP

(57) ABSTRACT

A soft tissue displacer tool can include a shaft that is elongate along a central axis, the shaft including a shaft body that defining a proximal end, a distal end that is spaced from the proximal end in a distal direction, and a central location that is disposed equidistantly between the proximal and distal ends. The shaft defines at least one inclined groove that 1) is inclined with respect to a plane that is normal to the central axis, and 2) revolves about the central axis, the groove terminating at a first end and a second end that is spaced from the first end along the distal direction, and the second end is spaced from the distal end. Soft tissue displacer tools are also described in which the shaft is cannulated. The soft tissue displacer tool can further include a guidance member, such as a K-wire, a trocar, or a bone punch.

22 Claims, 7 Drawing Sheets

(51) Int. Cl.
*A61B 17/17* (2006.01)
*A61B 17/02* (2006.01)
*A61B 17/00* (2006.01)
*A61B 17/34* (2006.01)
*A61B 17/32* (2006.01)
*A61B 90/00* (2016.01)

(52) U.S. Cl.
CPC ............... *A61B 2017/00685* (2013.01); *A61B 2017/320064* (2013.01); *A61B 2090/062* (2016.02)

(56) References Cited

U.S. PATENT DOCUMENTS

| | | | | |
|---|---|---|---|---|
| 4,830,000 A | * | 5/1989 | Shutt | A61B 17/1615 408/207 |
| 5,013,317 A | * | 5/1991 | Cole et al. | 606/96 |
| 5,098,435 A | | 3/1992 | Stednitz et al. | |
| 5,242,443 A | * | 9/1993 | Kambin | A61B 17/7007 606/249 |
| 5,374,270 A | * | 12/1994 | McGuire | A61B 17/15 606/104 |
| 5,676,545 A | | 10/1997 | Jones | |
| 5,686,673 A | * | 11/1997 | Kabis | G01N 1/12 73/863.31 |
| 5,833,628 A | * | 11/1998 | Yuan | A61B 10/025 600/567 |
| 6,197,031 B1 | * | 3/2001 | Barrette | A61B 17/155 606/311 |
| 6,306,142 B1 | * | 10/2001 | Johanson | A61B 10/025 606/79 |
| 6,312,432 B1 | | 11/2001 | Leppelmeier | |
| 7,048,477 B2 | * | 5/2006 | Abrams | A61B 17/1617 408/1 R |
| 2005/0273107 A1 | * | 12/2005 | Stevens | A61B 17/1615 606/916 |
| 2007/0270711 A1 | * | 11/2007 | Gil | A61B 10/025 600/567 |

FOREIGN PATENT DOCUMENTS

| | | |
|---|---|---|
| JP | 03-224553 A | 10/1991 |
| JP | 2003-245283 | 9/2003 |
| WO | WO 2007/0114553 | 10/2007 |
| WO | WO 2009/0066935 | 5/2009 |

OTHER PUBLICATIONS

Written Opinion issued for PCT/US2014/021501 received Jul. 7, 2014, 7 pages.

\* cited by examiner

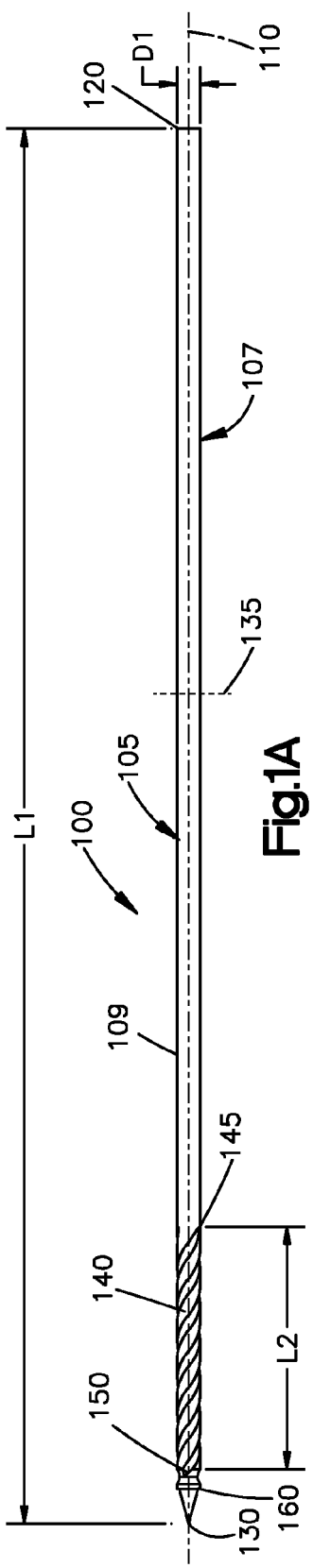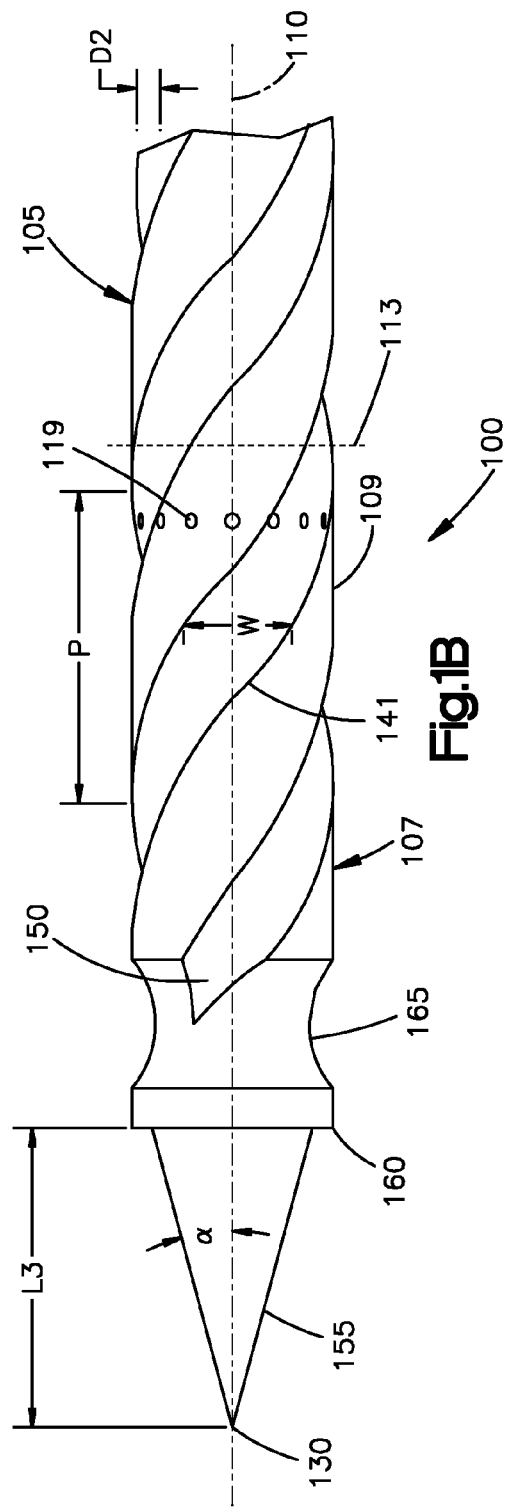
Fig.1A
Fig.1B

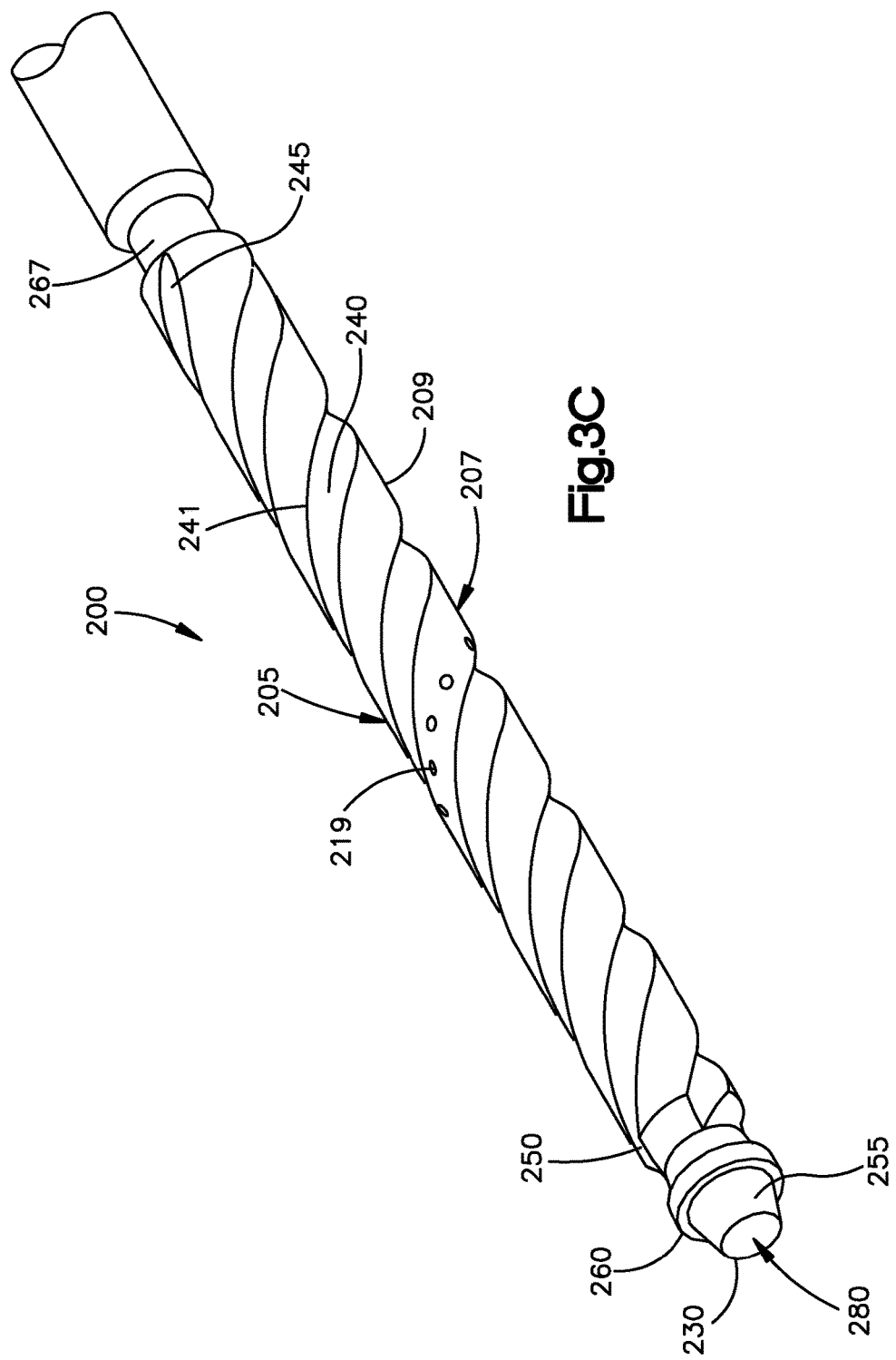

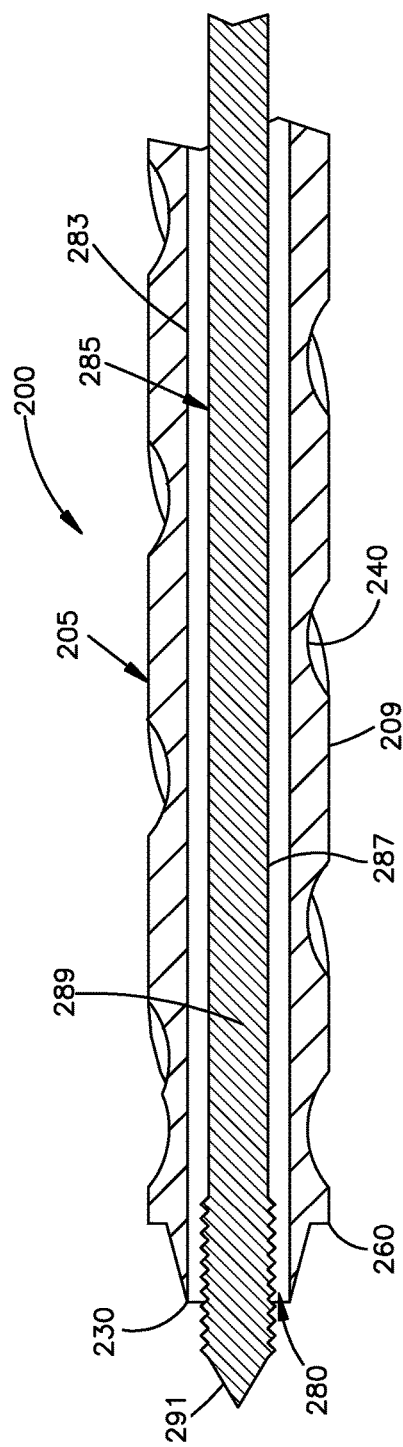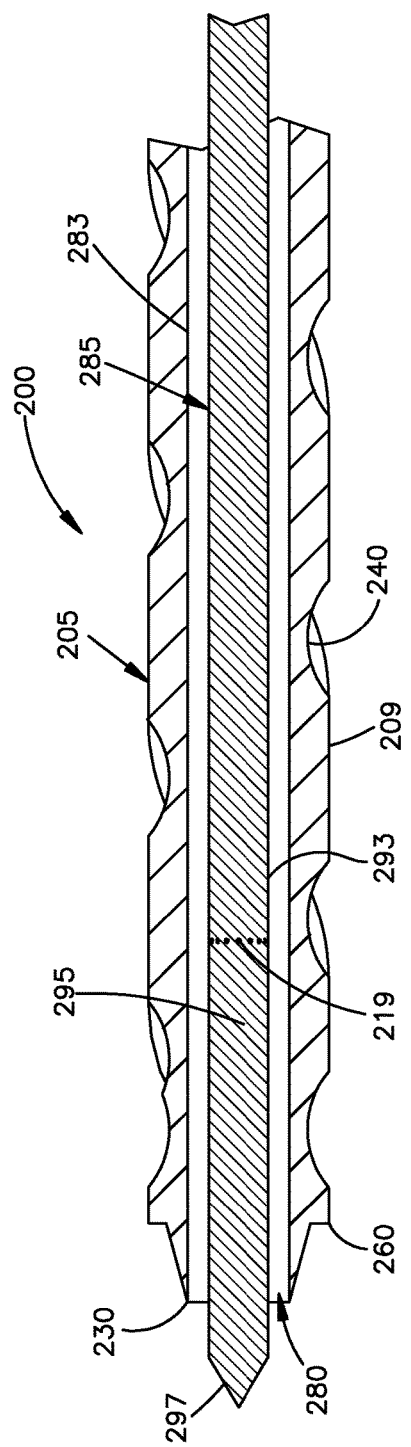
Fig. 4A
Fig. 4B

SOFT TISSUE DISPLACER TOOL WITH INCLINED GROOVE AND METHODS

TECHNICAL FIELD

The present disclosure relates to a tool for displacing soft tissue, such as when forming a recess in a bone, and also relates to a method for using the same.

BACKGROUND

In transtendon rotator cuff repairs using a conventional bone punch the surgeon drives the bone punch through the rotator cuff and into the bone. The bone punch may carry a visual marking which is viewed by the surgeon using a camera to determine when the punch has been driven to the desired depth. As the bone punch is driven through the rotator cuff and into the bone, the frictional forces between the bone punch and the rotator cuff cause the bone punch to carry the rotator cuff against the bone. The result is that the rotator cuff often obstructs the view of the camera to the bone punch.

It has been found that a helical groove on the body of a soft tissue displacer tool, including a bone punch having a visual marking, can be used to raise the rotator cuff away from the bone, restoring the line of sight between the camera to the bone punch.

SUMMARY

In an embodiment, a soft tissue displacer tool for moving soft tissue along an outer shaft surface of the tool can include a shaft. The shaft can be elongate along a central axis, and can include a shaft body having a proximal end, a distal end that is spaced from the proximal end in a distal direction, a central location that is disposed equidistantly between the proximal and distal ends, and an outer shaft surface. The outer shaft surface comprises at least one inclined groove that is recessed into the shaft body and 1) is inclined with respect to a plane that is normal to the central axis, and 2) revolves about the central axis, the groove terminating at a first end and a second end that is spaced from the first end along the distal direction, and the second end is spaced from the distal end along a proximal direction that is opposite the distal direction.

In an embodiment, a method of forming a hole in a bone includes inserting a shaft through a soft tissue and at least to the bone and, after the inserting step, rotating the shaft so as to cause the inclined groove to raise the soft tissue away from the bone. The shaft can be elongate along a central axis, and can include a shaft body having a proximal end, a distal end that is spaced from the proximal end in a distal direction, a central location that is disposed equidistantly between the proximal and distal ends, and an outer shaft surface. The outer shaft surface comprises at least one inclined groove that is recessed into the shaft body and 1) is inclined with respect to a plane that is normal to the central axis, and 2) revolves about the central axis, the groove terminating at a first end and a second end that is spaced from the first end along the distal direction, and the second end is spaced from the distal end along a proximal direction that is opposite the distal direction.

BRIEF DESCRIPTION OF THE DRAWINGS

The foregoing summary, as well as the following detailed description of illustrative embodiments of soft tissue displacer tool of the present application, will be better understood when read in conjunction with the appended drawings. For the purposes of illustrating the soft tissue displacer tool of the present application, there is shown in the drawings illustrative embodiments. It should be understood, however, that the application is not limited to the precise arrangements and instrumentalities shown. In the drawings:

FIG. 1A is a side elevation view of a soft tissue displacer tool constructed in accordance with one embodiment;

FIG. 1B is an enlarged side elevation view of a portion of the soft tissue displacer tool shown in FIG. 1A;

FIG. 3C is an enlarged perspective view of a portion of the shaft illustrated in FIG. 3B;

FIG. 4A is a sectional side elevation view of the enlarged portion of the shaft illustrated in FIG. 3C, and a guidance member in the form of a K-wire extending through the shaft.

FIG. 4B is a sectional side elevation view of the enlarged portion of the shaft illustrated in FIG. 3C, and a guidance member in the form of a trocar extending through the shaft.

DETAILED DESCRIPTION

Figure 1C:
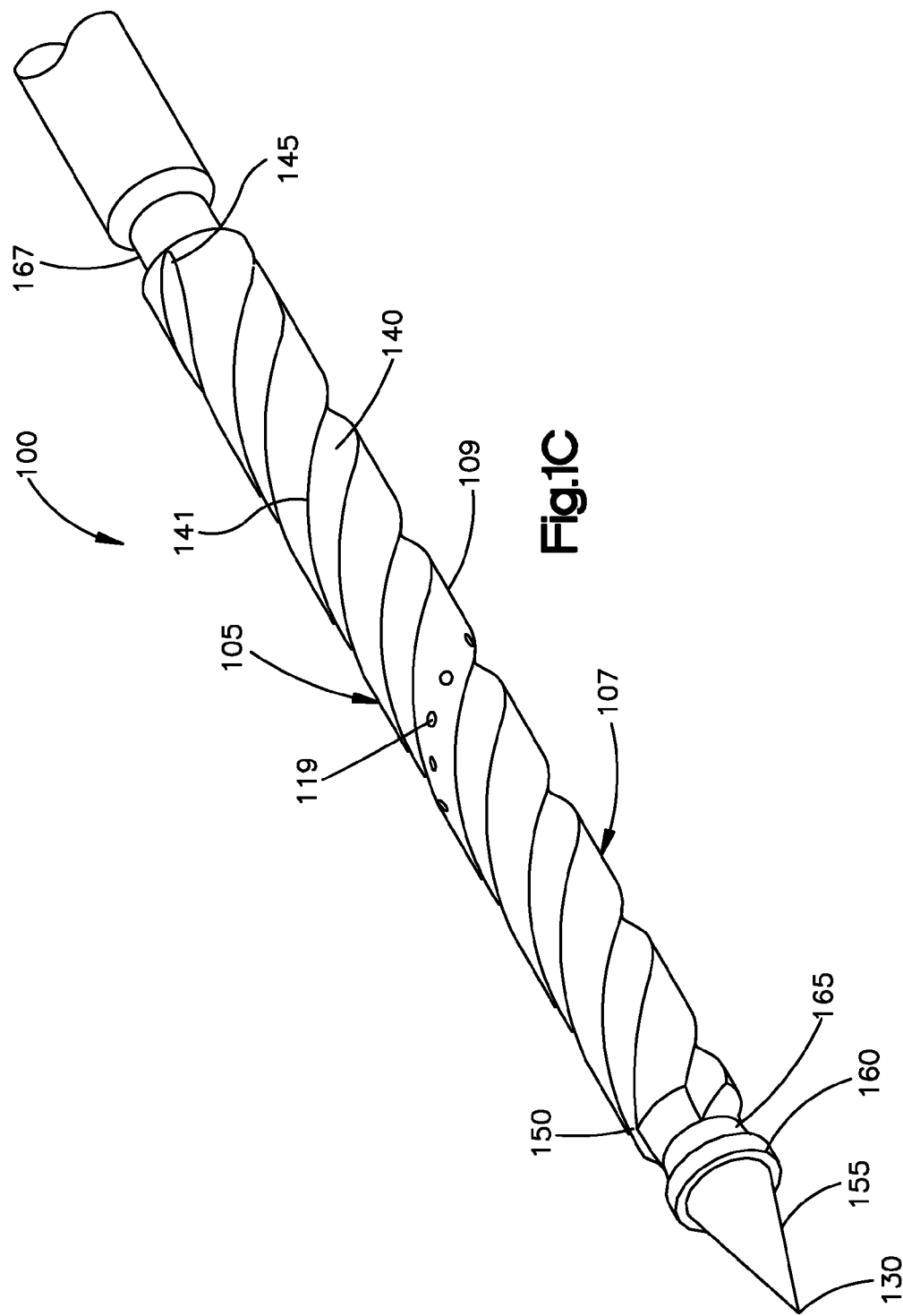
FIG. 1C is an enlarged perspective view of a portion of the soft tissue displacer tool shown in FIG. 1A.

Referring to FIGS. 1A-C, a soft tissue displacer tool 100 in accordance with one embodiment can include a shaft 105 having a shaft body 107. The shaft body 107 can be elongate generally along a central axis 110, which can be linear as illustrated, or otherwise shaped as desired. The shaft body 107 defines a proximal end 120 and a distal end 130 that is spaced from the proximal end 120 along the central axis. The shaft body 107 can further include a central location 135 that is disposed between the proximal end 120 and distal end 130 and is spaced approximately equidistant from the proximal end 120 and the distal end 130. For instance, the central location 135 can be located on the central axis 110. The term "proximal" and derivatives thereof are used herein to refer to a direction from the distal end 130 toward the proximal end 120, and the term "distal" and derivatives thereof are used herein to refer to a direction from the proximal end 120 toward the distal end 130. The shaft body 107 can be shaped substantially cylindrically as illustrated in FIG. 1A, or can assume other shapes, such as a polyhedron, as desired. The shaft body 107 can define an outer surface 109 that extends about the central axis 110. The shaft body 107 can have any length (L1) and diameter (D1) suitable for insertion through soft tissue and at least to the bone of a patient. The length (L1) and diameter (D1) can be chosen based on the size and location of the bone to be addressed in the surgical procedure. That is, for example, the length (L1) can be from about 3 inches to about 12 inches, preferably from about 5 to about 10 inches; and the diameter (D1) can be from about 0.05 inches to about 0.5 inches, preferably from about 0.075 inches to about 0.25 inches. In a non-limiting example, a shaft body 107 to be used in a rotator cuff repair can have a length (L1) that is in a range of from about 5 inches to about 9 inches, preferably from about 6.5 to about 8 inches, or that is about 7-7.5 inches. In a non-limiting example, a shaft body 107 to be used in a rotator cuff repair can have a diameter (D1) that is in a range of from about 0.10 inches to about 0.14 inches, or from about 0.11 inches to about 0.13 inches, or that is about 0.12 inches.

The shaft 105 can further define at least one groove 140 that extends into the shaft body 107, for instance into the outer surface 109 toward the central axis 110. The outer surface 109 can be substantially smooth between the groove sections 140. The outer surface 109 can be configured as one or more protrusions, for example wide threads, such that the groove 140 is defined between adjacent ones of the protrusions. The groove 140 can terminate at a location between the outer surface 109 and the central axis 110. The groove 140 is inclined with respect to a plane 113 that is normal to the central axis 110 and the groove 140 revolves about the central axis 110. Thus, the groove 140 extends along the outer surface 109, for instance circumferentially, as it travels along the proximal and distal directions. In accordance with the illustrated embodiment, as the groove 140 travels along the proximal direction, the groove can extend clockwise about the central axis 110 with respect to a proximally-oriented view from the distal end 130. Thus, as the groove 140 travels along the distal direction, the groove 140 can extend clockwise about the central axis 110 with respect to a distally-oriented view from the proximal end 120. It should be appreciated, of course, that the groove 140 can alternatively extend counter-clockwise about the central axis 110 with respect to a proximally-oriented view from the distal end 130 as the groove 140 travels along the proximal direction. In this regard, the groove 140 is a helical spiral shape along the shaft 105. Furthermore, in accordance with the illustrated embodiment, the shaft 105 can include a plurality of the grooves 140 that are circumferentially spaced, for instance equidistantly or variably, from each other along the outer surface 109. While the shaft 105 is illustrated as including two grooves 140 spaced 180 degrees from each other about the central axis 110, the shaft 105 can include as many grooves 140 as desired, such as one, two, three, four, or more grooves, that is one or a plurality of grooves. Each of the plurality of grooves 140 can be constructed as described with respect to the groove 140 herein.

The groove 140 terminates at a first or proximal end 145 and a second or distal end 150. Thus, the second end 150 is spaced apart from the first end 145 in the distal direction, and the first end 145 is spaced from the second end 150 in the proximal direction. The second end 150 can further be spaced from the distal end 130 of the shaft body 107 along the proximal direction, for instance at a location between the distal end 130 and the central location 135. The distance the second end 150 is spaced from the distal end 130 of the shaft body 107 can be chosen based on the application of the soft tissue displacement tool. In most applications, the second end 150 will be from about 0.05 inches to about 1.0 inch, preferably from about 0.1 inches to about 0.8 inches, and more preferably from about 0.2 inches to about 0.3 inches. In a non-limiting example useful for addressing rotator cuff surgical repair procedures, the distance the second end 150 is spaced from the distal end 130 of the shaft body 107 can be in a range of from about 0.05 inch to about 0.8 inches, or from about 0.1 inches to about 0.5 inches, or about 0.25 inches. The first end 145 can be disposed anywhere along the shaft body 107 as desired at a location proximal of the second end 150. For instance, the first end of the groove 145 can be disposed between the central location 135 and the second end of the groove 150, can be disposed between the central location 135 and the proximal end of the shaft 120, and can further extend to the proximal end of the shaft 120. The distance along the central axis 110 between the proximal end 145 and the distal end 150 of the groove can define a groove length (L2) that can be chosen based on the application of the soft tissue displacement tool. In most applications, the groove length (L2) will be from about 0.5 inches to about 10 inches, preferably from about 0.7 inches to about 5 inches, and more preferably from about 0.7 inches to about 4 inches. In a non-limiting example useful for addressing rotator cuff surgical repair procedures, a shaft body 107 can have a groove length (L2) that is in a range of from about 1 inch to about 1.4 inches, or from about 1.1 inches to about 1.3 inches, or that is about 1.2 inches.

With continuing reference to FIGS. 1A-C, the groove 140 can be configured as a helix having a consistent pitch P throughout at least a portion, such as an entirety, of its length. In other embodiments the groove 140 revolves around the central axis 110 and may have a varying pitch P. As used herein, a "helix" or a "helical" groove can have a consistent pitch P or a varying pitch P. The shaft body 107 can define an interface 141 between the groove 140 and the outer surface 109. The interface 141 can define an angle, a beveled edge, a rounded edge, or any suitably constructed structure that provides an interface between the outer surface 109 and the groove 140. The groove 140 can have a generally consistent depth D2, which can be measured from the outer surface 109 toward the central axis 110, and width W that can be measured from a first side of the groove 140 to a second side of the groove 140 along a direction that is about the central axis 110 along a plane that is oriented normal to the central axis 110. The depth D2 can be chosen based on the size and location within the body of the patient of the bone to be recessed. For example, the depth D2 can be from about 0.0005 inches to about 0.05 inches, and the width can be from about 0.01 to about 0.50 inches. For example, in a device to be used in rotator cuff repair, the groove 140 can have a depth D2 that is in a range of from about 0.005 inch to about 0.025 inch, or from about 0.010 inch to about 0.020 inch, or that is approximately 0.014 inch, with a width W of from about 0.08 to about 0.24 inches. It should be appreciated that the groove 140 can define any suitable alternative depth D2 and width W as desired. The groove 140 can have a curved cross-section, or a cross-section made up of a plurality of intersecting planes (e.g. rectangular or square). In a non-limiting example, a shaft body 107 to be used in a rotator cuff repair can have a groove 140 having a curved cross-section with a radius of curvature that is in a range of from about 0.01 inch to about 0.1 inch, or that is about 0.06 inch.

Still referring to FIGS. 1A-C, the distal end 130 of the shaft body 107 can include a tip 155. The tip 155 can be tapered in the distal direction. In some embodiments the tip 155 terminates in a point, while in other embodiments the tip 155 can be blunt. The tip 155 can be conical, pyramidal, polyhedral, or shaped like a frustum. The foregoing example tip shapes are illustrative and are not meant to be limiting. The tip 155 can be configured to be driven into or through soft tissue or bone, such as through the cortical wall of the bone and into the cancellous portion of the bone, as is described in more detail below. The tip 155 can have an angle (α) with respect to the central axis 110 and a length (L3) that can independently be chosen based on the application of the soft tissue displacement tool. In a non-limiting example, a shaft body 107 to be used in a rotator cuff repair can have a tip angled with respect to the central axis (α) that is in a range of from about 20° to about 40°, from about 25° to about 35°, or that is about 30°. In a non-limiting example, a shaft body 107 to be used in a rotator cuff repair can have a tip 155 having a length (L3) that is in a range of from about 0.10 inch to about 0.30 inch, or that is about 0.18 inch.

The shaft body 107 can further define a cutting edge 160 which, in one embodiment, is distal facing. The cutting edge 160 can define a shoulder that extends out with respect to the tip 155, for instance out from the tip 155, in a direction substantially normal to the central axis 110, which can also be referred to as a radial direction, regardless of whether the shaft body 107 is cylindrical or alternatively shaped. The cutting edge 160 can be annular or segmented as desired. Alternatively, the cutting edge 160 can extend out from the tip at any angle as desired with respect to the central axis 110. The cutting edge 160 can have a circular or polygonal perimeter extending about the central axis 110. The cutting edge 160 can be straight, jagged, serrated, or another configuration that is capable of cutting, punching, or otherwise being driven through soft tissue or bone, such as the cortical wall of the bone.

The shaft 105 can also carry a channel 165 that extends into the shaft body 107, for instance into the outer surface 109 toward the central axis 110. The channel 165 can terminate at a location between the outer surface 109 and the central axis 110. The channel 165 can extend along the outer surface 109 about the central axis 110, for instance circumferentially about the central axis 110. As the channel 165 revolves about the central axis 110, the channel 165 does not translate along the central axis 110 in either the proximal or distal directions. The channel can be disposed proximal of the tip 155 and distal of the groove 140 (e.g., between the tip 155 and the groove 140). In embodiments where the cutting edge 160 is present, the channel 165 can be disposed adjacent, for instance proximal, with respect to the cutting edge 160, such that the cutting edge 160 is disposed between the tip 155 and the channel 165. The channel 165 can have a curved cross-section, or a cross-section made up of a plurality of intersecting planes. The channel 165 can be designed to have the same or different depth and/or cross-sectional shape with respect to the groove 140. In a non-limiting example, a shaft body 107 to be used in a rotator cuff repair can have a channel 165 having a curved cross-section with a radius of curvature that is in a range from about 0.01 inch to about 0.1 inch, or that is about 0.06 inch.

The shaft body 107 can carry a visual marking 119 that is located a predetermined distance from the distal end 130 along the central axis 110, which can be a linear distance as described above. The distance of the visual marking 119 from the distal end 130 of the shaft can be predetermined based on the clinical situation in which the particular soft tissue displacer tool is designed to be used and can vary depending on the intended use of the soft tissue displacer tool. Ordinarily, once the visual marking 119 is positioned it is not varied by the user of the soft tissue displacer tool 100. The predetermined distance can correspond to the preferred depth of a recess formed in the bone when the depth indicated is driven into the bone, as is described in more detail below. Thus, a medical professional can use the visual marking 119 as a guide to gauge the depth to which the soft tissue displacer tool 100 has been inserted in the bone, and thereby gauge the depth of the recess in the bone into which the soft tissue displacer tool 100 has been inserted.

The shaft 105 can also carry a second channel 167 that extends into the shaft body 107, for instance into the outer surface 109 toward the central axis 110. The channel 167 can terminate at a location between the outer surface 109 and the central axis 110. The channel 167 can extend along the outer surface 109 about the central axis 110, for instance circumferentially about the central axis 110. As the channel 167 revolves about the central axis 110, the channel 167 does not translate along the central axis 110 in either the proximal or distal directions. The channel can be disposed proximal of the groove 140 (e.g., between the groove 140 and the proximal end 120). The channel 167 can have a curved cross-section, or a cross-section made up of a plurality of intersecting planes. The channel 167 can be designed to have the same or different depth and/or cross-sectional shape with respect to the groove 140.

Figure 2C:
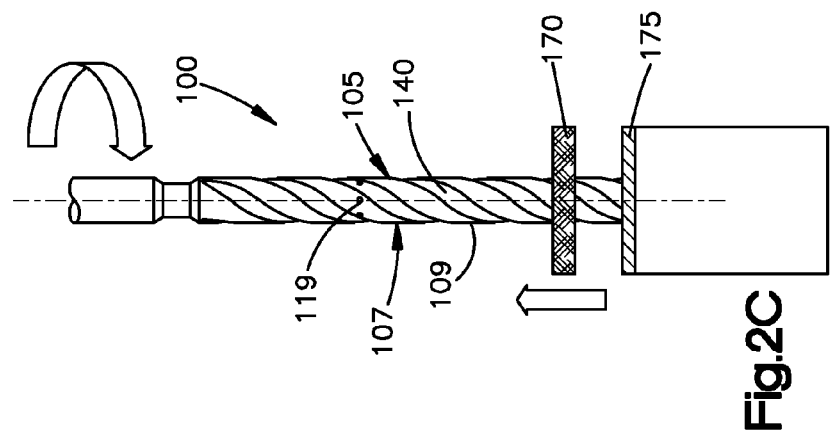
FIG. 2C is a side elevation view of the soft tissue displacer tool shown in FIG. 2 after being rotated and having lifted the soft tissue away from the bone.
Figure 2B:
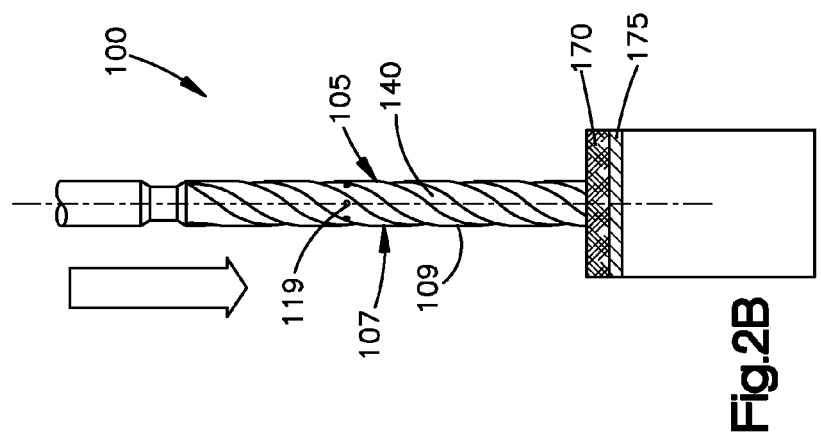
FIG. 2B is a side elevation view of the soft tissue displacer tool shown in FIG. 2 driven into a soft tissue and a bone, the soft tissue having been carried to the surface of the bone.
Figure 2A:
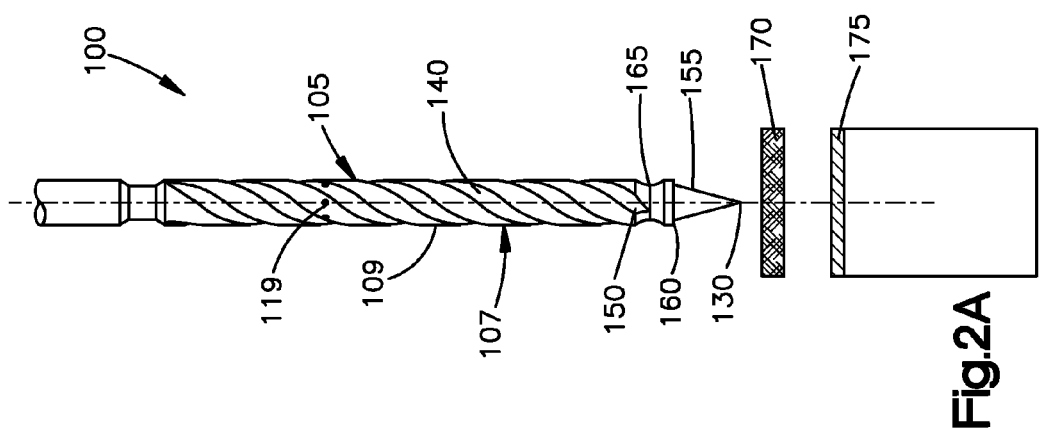
FIG. 2A is a side elevation view of the soft tissue displacer tool shown in FIG. 2 approaching a soft tissue and bone.

Referring now to FIG. 2A, a method of inserting the soft tissue displacer tool 100 into bone at a predetermined depth for future securement of soft tissue to the bone in the recess will now be described. For instance, in some procedures, such as the repair of a soft tissue, including a rotator cuff, the shaft 105 can be inserted through the soft tissue 170 and at least to the outer surface of the bone 175. In accordance with the illustrated embodiment, the shaft, for instance at distal end 130, which can be a tapered, or pointed, tip, can be driven through the soft tissue 170 toward the bone that underlies the soft tissue 170. Next, as illustrated in FIG. 2B, the distal end 130 of the shaft body 107 can be driven into the underlying bone 175. For instance, the distal end 130 can be punched, or driven substantially linearly without rotation, into the bone under a distally directed force that is applied to the shaft. The force can be an impacting force, such as that from a hammer or mallet, or can be a substantially constant force. Alternatively or additionally, the distal end 130 can be rotated in one direction, or back-and-forth, as a distal force applied to the shaft 105 drives the distal end 130 into the bone. Frictional forces between the outer surface 109 of the shaft body 107 and the soft tissue 170 can cause the soft tissue 170 to be carried with the shaft 105 toward, for instance to, the outer surface of the bone 175, which can obscure a view between the soft tissue and the bone (either by naked eye or by a surgical camera system). It will be appreciated that the bone depth is achieved when the visual marking 119 is in a predetermined proximity with respect to the bone, for instance inline with or adjacent the outer surface of the bone. Accordingly, it is desirable to provide an unobstructed view to the outer surface of the bone so as to ensure visibility of the visual marking 119 when the visual marking 119 is in the predetermined proximity with the outer surface of the bone.

Referring now to FIG. 2C, once the soft tissue displacer tool has been inserted into the bone 175, the shaft 105 can be rotated, which causes at least a portion of at least one of the grooves 140 to at least partially receive at least a portion of the soft tissue 170. Due to the incline of the grooves 140, as the shaft 105 is rotated, the grooves 140 apply a proximally-directed force to the soft tissue that cause the soft tissue 170 to move along the proximal direction with respect to the bone 175. Thus, the rotation of the shaft 105 causes the grooves 140 to lift the soft tissue 170 off of the bone 175. Otherwise stated, the grooves 140 are inclined such that by rotating the shaft 105 the one or more locations on the grooves 140 that contact the soft tissue 170 move along the shaft 105 in the proximal direction away from the bone 175. As illustrated in FIG. 2C, clockwise rotation of the shaft 105 causes the grooves 140 to lift the soft tissue 170 away from the bone 175. Alternatively, it should be appreciated that the grooves 140 can be configured such that counter-clockwise rotation of the shaft 105 causes the grooves 140 to lift the soft tissue 170 away from the bone 175. Because the soft tissue 170 is spaced from the bone 170, the portion of the shaft 105 disposed between the soft tissue 170 and the bone 175 can be visualized and the position of the visual marking 119 with respect to the bone 175 observed when the marking is on the portion of the shaft body 107 that is disposed between the soft tissue 170 and the bone 175. The soft tissue can be raised a sufficient height to allow a field of view to the visual marking. Depending on the physiology of the patient, the soft tissue 170 can be raised until it is tented, or pulled taut, to restore the field of view of the visual marking 119, while in other patients the visual marking 119 can be visualized without raising the soft tissue 170 to the point of being tented.

Figure 2F:
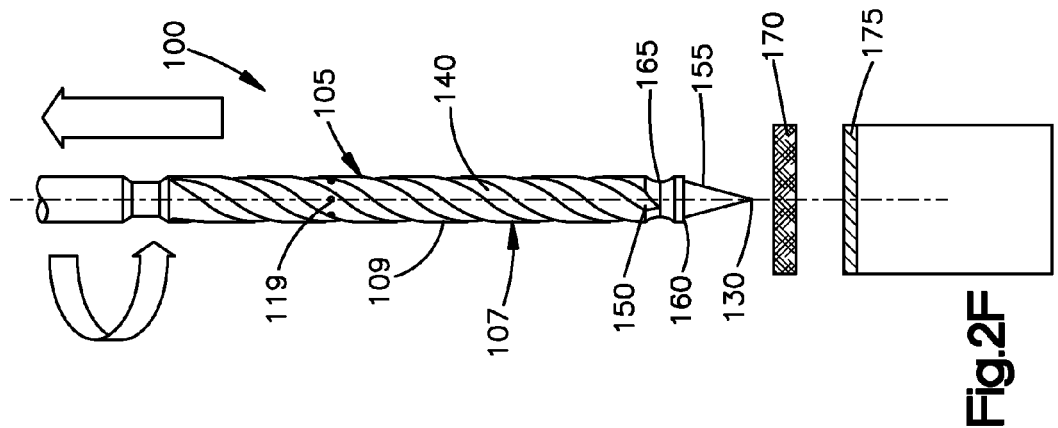
FIG. 2F is a side elevation view of the soft tissue displacer tool shown in FIG. 2A after being rotated and removed from the soft tissue and bone.
Figure 2E:
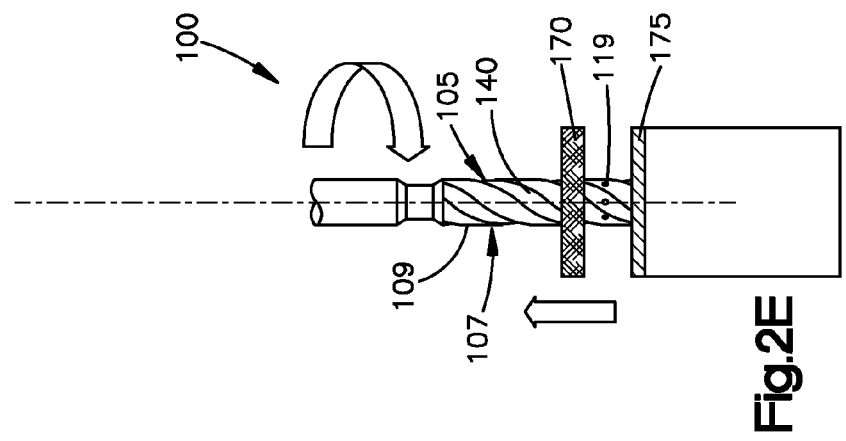
FIG. 2E is a side elevation view of the soft tissue displacer tool shown in FIG. 2 after being repeatedly driven into a soft tissue and rotated to lift the soft tissue away from the bone.
Figure 2D:
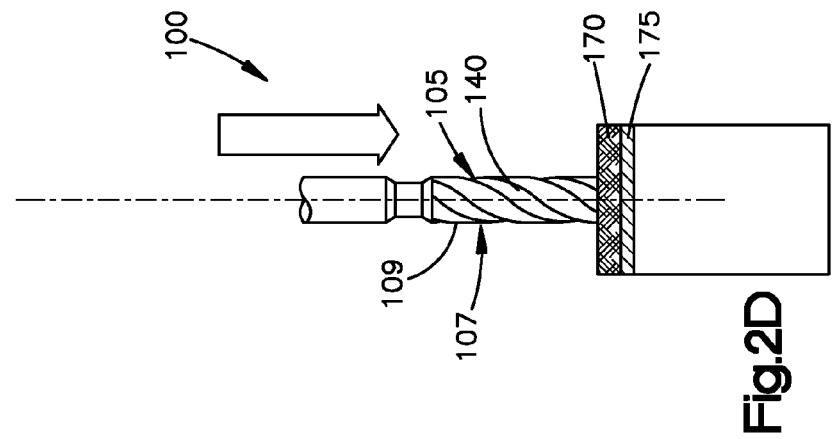
FIG. 2D is a side elevation view of the soft tissue displacer tool shown in FIG. 2 after being driven into a soft tissue and a bone to a deeper depth than shown in FIG. 2B.

After rotating the shaft 105, the visual marking 119 can be disposed between the soft tissue and the bone, and thus visually accessed by a camera or other imaging instrument whose field of view is between the soft tissue and the bone. A determination can be made as to the position of the visual marking 119 with respect to the predetermined proximity with respect to the bone 175. If the marking 119 is not yet in the predetermined proximity with respect to the bone 175, the shaft 105 can be further driven into the soft tissue 170 and into the bone 175, as illustrated in FIG. 2D. Referring to FIG. 2E, the shaft 105 can again be rotated to raise the soft tissue 170 away from the bone 175 as described above. The shaft 105 can be continuously driven into the bone 175 and subsequently rotated to lift the soft tissue 170 away from the bone 175 as desired until the visual marking 119 is in the predetermined proximity with respect to the bone 175, thereby indicating that the shaft 105 has been driven to the predetermined depth. A camera or other instrumentality can be used to assist the medical professional in viewing the visual marking. Once the recess having the desired depth has been created, the shaft 105 can be removed from the bone 175 by application of pulling or turning, or a combination of pulling and turning forces, as illustrated in FIG. 2F. For instance, the shaft 105 can be configured for removal by rotating the shaft 105 in a counterclockwise direction as viewed from the proximal end 120 toward the distal end 130, or can be configured for removal by rotating the shaft in a clockwise direction as viewed from the proximal end 120 toward the distal end 130.

It should be appreciated that while a soft tissue displacer tool has been described in accordance with one embodiment, the soft tissue displacer tool can be constructed in accordance with any suitable alternative embodiment as desired. For instance, while the shaft of the soft tissue displacer tool can be solid and have a pointed tip, the shaft of the soft tissue displacer tool can also be cannulated and used in combination with a guidewire or separate recess forming instrument.

Figure 3A:
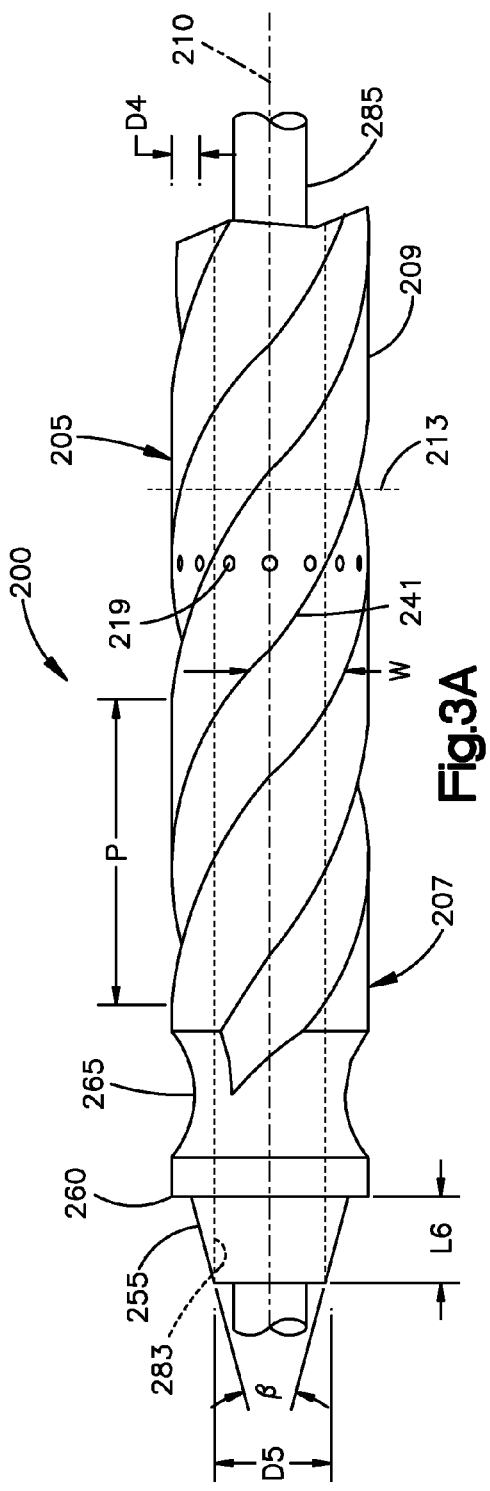
FIG. 3A is a side elevation view of a soft tissue displacer tool according to another embodiment, including a shaft and a guidance member configured to guide the shaft toward bone.
Figure 3B:
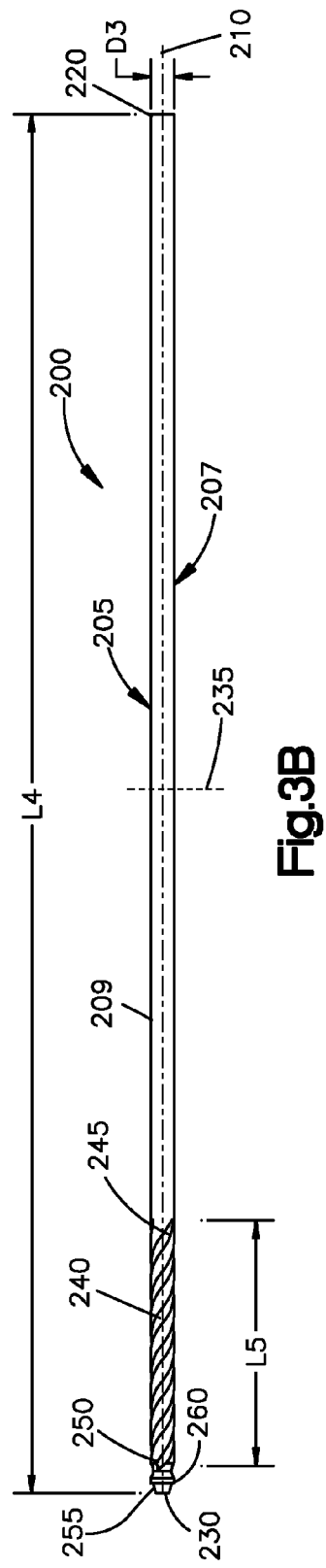
FIG. 3B is a side elevation view of the shaft illustrated in FIG. 3A.

Referring now to FIGS. 3A-3C, the soft tissue displacer tool 200 can include a cannulated shaft 205 that can be constructed as described above, but is further configured to be cannulated; thus the tool 200 can receive a guidance member 285 that can pierce soft tissue, and in some embodiments, can be inserted into underlying bone. For instance, the guidance member 285 can be configured to form a recess in the underlying bone (e.g., a self-cutting K-wire), or can be configured to be secured in a previously-formed recess in the underlying bone (e.g., a K-wire used after a drilling procedure), or can be configured to abut the bone (e.g., a trocar). As will be described in more detail below, the guidance member 285 can be advanced at least to the surface of the bone, and in some embodiments advanced or secured in the underlying bone, and the soft tissue displacer tool 200 can be rotated in the manner described above so as to lift the soft tissue off the bone in order to provide visual access to the visual marking 219.

The shaft 205 can thus include a shaft body 207. The shaft body 207 can be elongate generally along a central axis 210, which can be linear as illustrated, or otherwise shaped as desired. The shaft body 207 defines a proximal end 220, a distal end 230 that is spaced from the proximal end 220 along the central axis. The shaft body 207 can further include a central location 235 that is disposed between the proximal end 220 and distal end 230 and is spaced approximately equidistant from the proximal end 220 and the distal end 230. For instance, the central location 235 can be located on the central axis 210. The term "proximal" and derivatives thereof are used herein to refer to a direction from the distal end 130 toward the proximal end 220, and the term "distal" and derivatives thereof are used herein to refer to a direction from the proximal end 220 toward the distal end 230. The shaft body 207 can be shaped substantially cylindrically as illustrated in FIG. 3A, or can assume other shapes, such as a polyhedron, as desired. The shaft body 207 can define an outer surface 209 that extends about the central axis 210. The shaft body 207 can have any length (L4) and diameter (D3) suitable for insertion through soft tissue and at least to the bone of a patient and these dimensions can be the same as described above for length (L1) and diameter (D1). The shaft 205 can be made of any suitable material, including metals and plastics, and preferably is a transparent or translucent material, including, but not limited to, polycarbonate, acrylic, and polystyrene.

The shaft 205 can further define at least one groove 240 that extends into the shaft body 207, for instance into the outer surface 209 toward the central axis 210. The groove 240 can be similar to the groove 140 described above, and can take the same general shape, pattern, and number as the groove 140 described above.

The distance along the central axis 210 between the proximal end 245 and the distal end 250 of the groove can define a groove length (L5) that can be chosen based on the application of the soft tissue displacement tool. The length (L5) can be the same as described above for length (L2), and the depth (D4) can be the same as above depth (D2).

Still referring to FIGS. 3A-C, the distal end 230 of the shaft body 207 can include a tip 255. The tip 255 can be tapered in the distal direction. In one embodiment the tip 255 can be blunt and in some embodiments the tip 255 is shaped like a frustum or a polyhedron. The foregoing example tip shapes are illustrative and are not meant to be limiting. The tip 255 can be configured to be driven into or through soft tissue, as is described in more detail below. The tip 255 can have an angle ($\beta$) with respect to the central axis 210 and a length (L6) that can independently be chosen based on the application of the soft tissue displacement tool. In a non-limiting example, a shaft body 207 to be used in a rotator cuff repair can have a tip angled with respect to the central axis ($\beta$) in a range of from about 20° to about 40°, in a range from about 25° to about 35°, or is about 30°. In a non-limiting example, a shaft body 207 to be used in a rotator cuff repair can have a tip 155 having a length (L6) that is in a range of from about 0.01 inch to about 0.10 inch, or is about 0.06 inch.

The shaft body 207 can further define a cutting edge 260 which, in one embodiment, is distal facing. The cutting edge 260 can define a shoulder that extends out with respect to the tip 255, for instance out from the tip 255, in a direction substantially normal to the central axis 210, which can also be referred to as a radial direction, regardless of whether the shaft body 207 is cylindrical or alternatively shaped. The cutting edge 260 can be annular or segmented as desired. Alternatively, the cutting edge 260 can extend out from the tip at any angle as desired with respect to the central axis 210. The cutting edge 260 can have a circular or polygonal perimeter extending about the central axis 210. The cutting edge 260 can be straight, jagged, serrated, or another configuration that is capable of cutting, punching, or otherwise being driven through soft tissue or bone such as the cortical wall of the bone.

The shaft 205 can also carry a channel 265 that extends into the shaft body 207, for instance into the outer surface 209 toward the central axis 210. The channel 265 can terminate at a location between the outer surface 209 and the central axis 210. The channel 265 can extend along the outer surface 209 about the central axis 210, for instance circumferentially about the central axis 210. As the channel 265 revolves about the central axis 210, the channel 265 does not translate along the central axis 210 in either the proximal or distal directions. The channel can be disposed proximal of the tip 255 and distal of the groove 240 (e.g., between the tip 255 and the groove 240). In embodiments where the cutting edge 260 is present, the channel 265 can be disposed adjacent, for instance proximal, with respect to the cutting edge 260, such that the cutting edge 260 is disposed between the tip 255 and the channel 265. The channel 265 can have a curved cross-section, or a cross-section made up of a plurality of planes. The channel 265 can be designed to have the same or different depth and/or cross-sectional shape with respect to the groove 240. In a non-limiting example, a shaft body 207 to be used in a rotator cuff repair can have a channel 265 having a curved cross-section with a radius of curvature that is in a range from about 0.01 inch to about 0.1 inch, or about 0.06 inch.

The shaft body 207 can carry a visual marking 219 that is located a predetermined distance from the distal end 230 along the central axis 210, which can be a linear distance as described above. The distance of the visual marking 219 from the distal end 230 of the shaft can be predetermined based on the clinical situation in which the particular soft tissue displacer tool is designed to be used and can vary depending on the intended use of the soft tissue displacer tool. Ordinarily, once the visual marking 219 is positioned it is not varied by the user of the soft tissue displacer tool 200. The predetermined distance can correspond to the preferred depth of a recess formed in the bone when the depth indicated is driven into the bone, as is described in more detail below. Thus, a medical professional can use the visual marking 219 as a guide to gauge the depth to which the soft tissue displacer tool 200 has been inserted in the bone, and thereby gauge the depth of the recess in the bone into which the soft tissue displacer tool 200 has been inserted. Alternatively, in embodiments in which the shaft body 207 is made of a transparent or translucent material, a guidance member 285 or other instrument received in the opening 280 of the shaft body 207 can carry a visual marking 219 that is located a predetermined distance from the distal end of the guidance member 285 or other instrument.

The shaft 205 can also carry a second channel 267 that extends into the shaft body 207, for instance into the outer surface 209 toward the central axis 210. The channel 267 can terminate at a location between the outer surface 209 and the central axis 210. The channel 267 can extend along the outer surface 209 about the central axis 210, for instance circumferentially about the central axis 210. As the channel 267 revolves about the central axis 210, the channel 267 does not translate along the central axis 210 in either the proximal or distal directions. The channel can be disposed proximal of the tip 255 and the groove 240 (e.g., between the groove 240 and the proximal end 220). The channel 267 can have a can have a curved cross-section, or a cross-section made up of a plurality of intersecting planes. The channel 267 can be designed to have the same or different depth and/or cross-sectional shape with respect to the groove 240.

Still referring to FIGS. 3A-C, the shaft 205 can be cannulated so as to define an opening 280 that extends through the shaft body 207 generally along the central axis 210 from the proximal end 220 to the distal end 230. The opening 280 can further be positioned centrally with respect to the central axis 210, and can be sized and shaped as desired so as to receive the guidance member 285 therein. Thus, it should be appreciated that the shaft body 207 includes an inner surface 283 that extends from the proximal end 220 to the distal end 230 and defines the opening 280. The inner surface 283 can be shaped substantially cylindrically, or can assume other shapes, such as a polyhedron, as desired. The inner surface 283 can have a diameter (D5) that is sized smaller than the diameter of the shaft body (D3) and large enough to receive a guidance member 285. In a non-limiting example, a shaft body 207 to be used in a rotator cuff repair can have an opening 280 defined by an inner surface 283 having a diameter (D5) that is in the range of from about 0.05 inch to about 0.15 inch or from about 0.05 inch to about 0.10 inch or that is about 0.07 inch.

Referring to FIGS. 4A-B, and as described above, the soft tissue displacer tool 200 can also include a guidance member 285 that has a proximal end, a distal end, and is elongated along a central axis, which can be linear as illustrated, or otherwise shaped as desired. The guidance member 285 can be constructed as desired, and can be configured to be advanced at least to the surface of the underlying bone, and in some embodiments advanced or secured in the underlying bone. For instance, as illustrated in FIG. 4A, the guidance member 285 constructed in accordance with one embodiment can be configured as a K-wire (Kirschner wire) 287 having a body 289 and a tip 291 that extends distally from the body 289. The tip 291 can be tapered along the distal direction, and can define a pointed tip as desired. The K-wire can have a pointed tip that is capable of piercing soft tissue and/or bone, such as the cortical wall of the bone, and being driven into the cancellous portion of the bone. For example, the K-wire tip shape can include a diamond tip or a trocar tip. The K-wire 287 can further be threaded at a location proximal to the tip 291, or can be smooth or devoid of threading. Accordingly, an opening can be pre-drilled in the bone, and the K-wire 287 can be inserted into the pre-created opening. If threaded, the K-wire can be rotated so as to threadedly attach to the bone. Alternatively, a drilling instrument can pre-create the opening. Alternatively still, the tip 291 of the K-wire 287 can be driven into the bone so as to create the opening. If threaded, the K-wire 287 can be subsequently rotated so as to threadedly attach to the bone. Thus, the K-wire 287 can be secured in the bone at a location that defines the recess to be formed. It should thus be appreciated that the guidance member 285 can be configured to be advanced into the bone, for example it can form an opening in the bone, or can be secured in the bone, for instance within a pre-drilled opening.

In some procedures, such as the repair of a soft tissue, including a rotator cuff, the guidance member 285, such as the K-wire 287, of the soft tissue displacer tool 200 can be introduced through the soft tissue and advanced or secured into the bone. For instance, the K-wire 287 can be advanced or secured in a pre-drilled opening or driven into the bone in the manner described above. If the K-wire is unthreaded, the K-wire 287 can be press-fit in the bone. Thus, the K-wire 287 can be implanted by any method known in the art, including driving, hammering, drilling, or screwing. It should be appreciated that the K-wire 287 can be advanced into or secured to the bone either while disposed in the opening 280 of the shaft 205, or outside the shaft 205. Thus, the method can include the step of placing the shaft 205 over the K-wire 287 such that the K-wire 287 extends through the opening 280 before or after advancement or securement of the K-wire 287 to the bone. Once the K-wire 287 has been advanced into or secured to the bone and further extends through the opening 280, the shaft 205 can be inserted through the soft tissue and to the bone along the K-wire 287.

It is appreciated that as the K-wire 287 is driven into the bone, frictional forces between the outer surface of the K-wire 287 and the soft tissue can cause the soft tissue to be carried with the K-wire 287 toward or to the outer surface of the bone. It is further appreciated that, in instances where the soft tissue was not carried to the bone during securement of the K-wire 287, frictional forces between the outer surface 209 of the shaft 205 and the soft tissue can cause the soft tissue to be carried with the shaft 205 to the outer surface of the bone as the shaft 205 is driven to the bone. Thus, when the K-wire 287 is secured in the bone, and the shaft 205 has been driven to the bone, the soft tissue can prevent visual access to the visual marking 219.

Thus, the shaft 205 can be driven into the bone to a sufficient depth such that the groove 240 is aligned with the soft tissue. Accordingly, the shaft 205 can be rotated in the manner described above with respect to the soft tissue displacer tool 100 so as to lift the soft tissue off of the bone. The position of the visual marking 219 can thus be assessed in the manner described above, and the shaft can further be driven into the bone and subsequently rotated so as to lift the soft tissue away from the bone as many times as desired so as to visually confirm that the soft tissue displacer tool 200 has been driven into the bone at the predetermined depth. A camera or other imaging system whose field of view is between the bone and the lifted soft tissue can provide an image of the visual marking 219 and the bone. Once the visual marking 219 has been aligned in the desired proximity with respect to the bone, the shaft 205 can be removed by pulling or turning, or a combination of pulling and turning as described above. The K-wire 287 can be removed from the bone before or after removal of the shaft 205.

Referring now to FIG. 4B, the guidance member 285 constructed in accordance with another embodiment can be configured as a trocar 293 having a body 295 and a tip 297 that extends distally from the body 295. The tip 297 can be tapered along the distal direction, and can define a pointed tip as desired. The tip 297 can be pointed and capable of piercing soft tissue. In some embodiments, the tip 297 can be capable of piercing the bone, such as the cortical wall of the bone, and being driven into the cancellous portion of the bone. Accordingly, the tip 297 of the trocar 293 can be driven into the soft tissue and the trocar 293 can further be driven at least to the surface of the bone or be driven into the bone to the desired depth. The trocar itself can be solid or can be cannulated to receive a guidewire. It should be appreciated that the trocar can carry the visual marking 219, and the shaft shaft 205 can be transparent or translucent so that the visual marking 219 carried by the trocar 293 is visible through the shaft 205. Alternatively, the trocar 293 can be used to pierce the soft tissue and carry the shaft 205 at least to the surface of the underlying bone. The trocar 293 can be removed from the opening 280 of the shaft 205 and an instrument, such as a bone punch, can be inserted into the opening 280 of the shaft 205. The instrument, such as a bone punch, can carry a visual marking 219 that is a predetermined distance from the distal end of the instrument. Accordingly, the shaft 205 can be made of a transparent or translucent material, including, but not limited to, polycarbonate, acrylic, and polystyrene, such that the visual marking 219 on the instrument can be seen through the shaft 205 when the instrument 285 is disposed within the opening 280 of the shaft 205.

During operation, the trocar 293 can be driven into the bone as described above. The trocar 293 can be driven into the bone before or after insertion of the trocar 293 into the opening 280. If the trocar 293 is driven into the bone prior to insertion into the opening 280, the shaft 205 can then be placed over the trocar 293 such that the trocar extends at least into or through the opening 280. Next, the shaft 205 can be driven along the trocar 293 until the distal end 230 is placed against the bone. Alternatively, the trocar 293 can be driven through the soft tissue and at least to the surface of the bone while disposed in the opening 280 of shaft 205. Frictional forces between the outer surface 209 of the shaft 205 and the soft tissue can cause the soft tissue to be carried with the shaft 205 to the outer surface of the bone. The soft tissue can be lifted away from the bone by rotating the shaft 205 in the manner described above until a desired field of view of the camera or other imaging device is directed between the soft tissue and the bone. The trocar can be removed from the opening 280 of the shaft 205 and an instrument can be inserted into the opening 280 of the shaft 205. The trocar 293 can be removed from the opening 280 of the shaft 205 before or after the shaft 205 has been rotated to raise the soft tissue away from the bone. Once the instrument is inserted into the opening 280 of shaft 205 the shaft 205 can be rotated to raise the soft tissue if the soft tissue is positioned so as to interfere with the field of vision of marking 219 on the instrument. The instrument can be driven into the bone and because the shaft 205 is in contact with the soft tissue, and the instrument is driven through the shaft 205, the step of driving the instrument into the bone does not cause the soft tissue to be carried toward the bone. The instrument and the shaft 205 can then be removed from the bone.

It should further be appreciated that in other applications, the soft tissue displacer tools 100 and 200 can be used to form a recess in a bone and to measure the depth of a recess in a bone in accordance with other methods. For instance, in instances where the soft tissue has been severed, and thus will not be carried along with the shaft toward the outer surface of the bone, the soft tissue displacer tool can be inserted into the bone and a medical professional can view the visual marking to determine the depth to which the soft tissue displacer tool has been inserted, and thereby determine the depth of the recess in the bone. The soft tissue displacer tool can be driven further into the bone and the visual marking viewed repeatedly until the soft tissue displacer tool has been inserted into the bone a depth commensurate with the predetermined distance between the visual marking and the distal end 130, 230.

In some procedures, such as repair of a soft tissue, including a rotator cuff, the medical professional will first complete the tear and insert the soft tissue displacer tool 100, 200 through the tear and into the bone. As described above, the medical professional can view the visual marking to determine the depth of the recess in the bone. The medical professional can repeat the steps of driving the soft tissue displacer tool into the bone and, if a visual marking is present, viewing the visual marking. When the soft tissue displacer tool has been inserted to the predetermined distance or the desired depth into the bone, the soft tissue displacer tool can be removed by pulling or turning, or a combination of pulling and turning. As illustrated in FIG. 1C, a soft tissue displacer tool 100 having a groove 140 that is clockwise as viewed proximally from the distal end, can be removed by rotating the bone recess indicator in a counterclockwise direction as viewed proximally from the distal end, either alone or in combination with the application of a proximally directed force to the shaft. It should be understood that a soft tissue displacer tool having a groove that is left-handed is well suited for removal by rotating the bone recess indicator in a counterclockwise direction as viewed from the proximal end.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

What is claimed is:

1. A soft tissue displacer tool for moving soft tissue away from bone, the soft tissue displacer tool comprising:
    a one-piece shaft that is elongate along a central axis, the shaft including a shaft body having a proximal end, a distal end that is spaced from the proximal end in a distal direction, and an outer shaft surface, the distal end defining a tip having a smooth outer tip surface that revolves an entire revolution about the central axis;
    wherein the shaft defines at least one helical groove that is recessed into the outer shaft surface toward the central axis and revolves about the central axis so as to define at least one helical protrusion that defines the outer surface of the shaft, whereby the at least one helical groove is defined between adjacent revolutions of the at least one protrusion about the central axis, and the helical groove (1) is inclined with respect to a plane that is normal to the central axis, and 2) terminates at a first end and a second end that is spaced from the first end along the distal direction, and the second end is spaced from the distal end along a proximal direction that is opposite the distal direction, and
    wherein the outer shaft surface revolves about the central axis at a fixed radius from the central axis as it extends along an entire circumferential distance between adjacent revolutions of the helical groove;
    a plurality of visual markings carried by the shaft at a fixed location between the first end of the helical groove and the second end of the helical groove, wherein the visual markings are visually accessible at the outer surface,
    wherein the shaft includes a distal facing cutting edge located between the second end of the at least one helical groove and the tip, the tip extends away from the cutting edge in the distal direction, the cutting edge extends out with respect to the tip in a direction away from the central axis, and the second end of the helical groove is spaced from the cutting edge in the proximal direction, and
    wherein the outer surface at the at least one protrusion is substantially smooth, such that the helical groove is configured to cause the soft tissue to move away from bone in the proximal direction as the shaft is rotated in the soft tissue once the soft tissue displacer has been driven into the bone.

2. The soft tissue displacer tool according to claim 1, wherein the tip is tapered and pointed.

3. The soft tissue displacer according to-claim 2, wherein the tapered pointed tip has a smooth outer surface.

4. The soft tissue displacer according to-claim 3, wherein the tip is non-cannulated.

5. The soft tissue displacer tool according to claim 1, wherein the tip is frustum-shaped.

6. The soft tissue displacer tool according to claim 1, wherein the helical groove is oriented so as to extend clockwise around the outer shaft surface as the groove extends in a proximal direction that is opposite the distal direction from a view from the distal end toward the proximal end.

7. The soft tissue displacer tool according to claim 1, wherein the shaft is cannulated so as to define an opening that extends along the central axis from the proximal end to the distal end.

8. The soft tissue displacer tool according to claim 7, wherein the shaft comprises a transparent or translucent material.

9. The soft tissue displacer tool according to claim 7, further comprising a guidance member sized to be received in the opening such that the shaft is rotatable with respect to the guidance member, the guidance member configured to pierce a soft tissue.

10. The soft tissue displacer tool according to claim 9, wherein the guidance member is configured to be advanced into a bone.

11. The soft tissue displacer tool according to claim 9, wherein the guidance member comprises one of a K-wire, a trocar, and a bone punch.

12. The soft tissue displacer tool according to claim 1, wherein the helical groove is has a constant depth along a direction from the outer surface toward the central axis, such that the helical groove is configured to cause the soft tissue to ride along the outer surface in the proximal direction as the shaft is rotated in the soft tissue.

13. The soft tissue displacer tool according to claim 1, wherein the protrusions extend continuously along a plurality of revolutions about the central axis.

14. The soft tissue displacer tool according to claim 1, wherein the shaft body is cylindrical.

15. The soft tissue displacer as recited in claim 1, wherein the shaft defines a circumferential channel that extends into the outer shaft surface toward the central axis along an entire revolution about the central axis.

16. The soft tissue displacer as recited in claim 15, wherein the distal facing cutting edge is located between the circumferential channel and the tip.

17. The soft tissue displacer as recited in claim 16, wherein at least a portion of the circumferential channel is disposed between the second end of the helical groove and the cutting edge.

18. A soft tissue displacer tool for moving soft tissue away from bone, the soft tissue displacer comprising:
   a transparent cannulated shaft that is elongate along a central axis, the shaft including a shaft body having a proximal end, a distal end that is spaced from the proximal end in a distal direction, and a tip at the distal end, wherein the cannulated shaft defines an outer shaft surface;
   wherein the shaft defines at least one helical groove that is recessed into the outer shaft surface toward the central axis and revolves about the central axis so as to define at least one protrusion that defines the outer surface of the shaft and extends continuously along a plurality of revolutions about the central axis, whereby the at least one helical groove is defined between adjacent revolutions of the protrusions about the central axis, and the at least one helical groove (1) is inclined with respect to a plane that is normal to the central axis, and 2) terminates at a first end and a second end that is spaced from the first end along the distal direction, and the second end is spaced from the distal end along a proximal direction that is opposite the distal direction; and
   a guidance member sized to be received in the cannulated shaft so as to extend out from the tip of the shaft along the central axis, wherein the cannulated shaft is rotatable with respect to the guidance member about the central axis, the guidance member comprises a plurality of markings at a fixed location of constant diameter on the guidance member, and the markings are visually accessible through the transparent cannulated shaft at an outer surface of the guidance member.

19. The soft tissue displacer tool according to claim 18, wherein the guidance member comprises one of a k-wire, a trocar, and a bone punch.

20. The soft tissue displacer according to claim 18, wherein the guidance member comprises a threaded tip.

21. The soft tissue displacer according to claim 18, wherein the guidance member has a tip that has a smooth outer surface.

22. The soft tissue displacer according to claim 18, wherein the shaft is a one-piece shaft that further includes a distal facing cutting edge located between the second end of the at least one groove on the outer shaft surface and the tip, the cutting edge extends out with respect to the tip in a direction away from the central axis, the tip extends away from the cutting edge in the forward direction, and the second end of the groove is spaced from the cutting edge in the proximal direction.

* * * * *